United States Patent [19]

Shimizu et al.

[11] 4,339,360

[45] Jul. 13, 1982

[54] PARTICLES OF ACTIVATED OXIDIZED POLYSACCHARIDE SUBSTANCE COATED WITH INACTIVE PROTECTIVE LAYER AND METHOD FOR MANUFACTURE THEREOF

[75] Inventors: Toshimi Shimizu; Shoei Fujishige; Akira Okada, all of Yokohama, Japan

[73] Assignees: Agency of Industrial Science & Technology; Ministry of International Trade & Industry, both of Tokyo, Japan

[21] Appl. No.: 129,335

[22] Filed: Mar. 11, 1980

[30] Foreign Application Priority Data

Mar. 31, 1979 [JP] Japan .................................. 54/39226

[51] Int. Cl.$^3$ .......................... C08L 1/08; C08L 3/04; A61K 9/36; A61K 9/40
[52] U.S. Cl. ...................................... 524/28; 523/205; 424/16; 424/20; 424/35; 424/36; 424/37; 428/407; 525/936; 525/54.21; 525/54.23; 525/54.25; 106/126; 106/130; 106/162; 524/35; 524/48; 524/49; 524/54
[58] Field of Search ................ 106/126; 260/17.4 CL; 424/16, 20, 33, 35, 37

[56] References Cited

U.S. PATENT DOCUMENTS

| | | | |
|---|---|---|---|
| 2,390,088 | 12/1945 | Fox et al. | 424/35 |
| 3,016,308 | 1/1962 | Macaulay | 101/DIG. 1 |
| 3,647,624 | 3/1972 | Evenson | 435/2 |
| 3,725,113 | 4/1973 | Chang | 424/36 |
| 3,886,084 | 5/1975 | Vassiliades | 424/37 |
| 3,943,238 | 3/1976 | Kobayashi et al. | 424/37 |
| 3,956,172 | 5/1976 | Saeki et al. | 424/37 |
| 4,010,038 | 3/1977 | Iwasaki et al. | 106/26 |
| 4,205,060 | 5/1980 | Monsimer et al. | 424/16 |
| 4,230,809 | 10/1980 | Heinrich et al. | 424/16 |

Primary Examiner—John Kight, III
Assistant Examiner—N. M. Nutter
Attorney, Agent, or Firm—Oblon, Fisher, Spivak, McClelland & Maier

[57] ABSTRACT

Particles of active substance each comprising a core of a high molecular substance containing an aldehyde group and a coat applied to the aforementioned core and formed of the reaction product of the aforementioned aldehyde group-containing high molecular substance with a high molecular substance containing active hydrogen, which particles are manufactured by causing particles of the aforementioned aldehyde group-containing high molecular substance to assume a swelled state and allowing the swelled particles to be reacted upon by the aqueous solution of the aforementioned active hydrogen-containing high molecular substance.

11 Claims, No Drawings

PARTICLES OF ACTIVATED OXIDIZED POLYSACCHARIDE SUBSTANCE COATED WITH INACTIVE PROTECTIVE LAYER AND METHOD FOR MANUFACTURE THEREOF

BACKGROUND OF THE INVENTION

1. Field of the Invention

This invention relates to particles of activated substance coated with an inactive protective layer and to a method for the manufacture thereof.

2. Description of the Prior Art

Generally when a substance possessing an active group is put to use in a solid state as in the form of particles, for example, there is a possibility that the active group present on the surface of such solid particles will produce an undesirable side effect. When dialdehyde starch having the aldehyde group as its active group is used for the removal of urea, ammonia and lower amines from the blood or body fluid, for example, the active aldehyde group distributed on the surface of the starch particles comes into contact with the blood or body fluid and readily reacts with many effective components contained in such fluid. When the dialdehyde starch is orally administered in an effort to eliminate urea, ammonia, etc. from within the intestinal tract, the active aldehyde group present on the surface of the starch particles readily reacts not only with the amino groups of the protein molecules forming the inner walls of the oral cavity, the gastric tract and other digestive organs but also with the amino groups resulting from the digestive decomposition of food. These side reactions are hardly negligible.

With a view to overcoming such drawbacks, particulate solid substances (such as oxidized starch) simply coated physically with microcapsules of ethyl cellulose have been proposed as described in the article "Removal of Uremic Waste Metabolites from the Intestinal Tract by Encapsulated Carbon and Oxidized Starch" of the Transaction of American Society Artif. Int. Organs, 17, 229~(1971), written by R. E. Sparks, N. S. Mason, P. M. Meier, M. H. Litt, and O. Lindan. These particles, however, have the disadvantage that the microcapsules applied as the coat thereto are incomplete and, therefore, allow the active aldehyde group distributed on the surface of the particles to be partially exposed through breaks in the coat and left to give rise to undesirable side reaction.

SUMMARY OF THE INVENTION

An object of this invention is to provide particles of active substance with protection against producing the side reactions which are otherwise caused by the active group present on the surface of the particles of active substance possessing the active group.

Another object of this invention is to provide a method for the manufacture of particles of active substance protected against producing the undesirable side reactions which are otherwise possibly caused by the active group present on the surface of the particulate active substance possessing the active group.

To accomplish the objects described above according to the present invention, there are provided particles of active substance each comprising a core formed of a high molecular substance containing an aldehyde group and an inactive protective layer coating the surface of the core and formed of the reaction product of the aforementioned high molecular substance with a high molecular substance containing active hydrogen. The particles of the present invention are produced by causing particles of a high molecular substance containing an aldehyde group to assume a swelled state and subsequently allowing the swelled particles to react with the aqueous solution of a high molecular substance containing active hydrogen.

DETAILED DESCRIPTION OF THE PREFERRED EMBODIMENT

The particles of active substance of the present invention comprise cores formed of a high molecular substance containing an aldehyde group and an inactive protective layer coating the surface of the cores and formed of the reaction product of the aforementioned high molecular substance with a high molecular substance containing active hydrogen. Unlike the ordinary particles which are simply coated physically with microcapsules, the particles of this invention have the surface of their cores coated with a layer which is bound fast to the aforementioned surface by the chemical union between the substance of the layer and the active group of the substance of the cores distributed on the surface. The portion of the active group of the substance of the cores which is distributed within the cores is retained in its unimpaired state.

The particles of active substance of the present invention are produced by causing particles of a high molecular substance containing an aldehyde group to assume a swelled state and subsequently allowing the swelled particles to react with the aqueous solution of a high molecular substance containing active hydrogen.

The active group-containing particles to be used in the present invention are the particles of high molecular substances containing an aldehyde group and possessing an ability to be swelled with water. Examples are the particles of high molecular compounds generally called dialdehyde derivatives and obtained by oxidizing, with a periodic acid, polysaccharides such as cellulose, starch, cross-linked dextrans, dextrins, mannans and alginic acid which possess two or more adjoining hydroxyl groups within the molecular units thereof.

The active hydrogen-containing high molecular substances to be used for the formation of the coating layer of the particles in the present invention are high-molecular substances containing a hydroxyl group or amino group. Examples are albumins, gelatins and other similar proteins, and polyvinyl alcohols, polyacrylamide, polymethacrylamide and other similar high molecular compounds. According to this invention, the particles of active substance are obtained by causing the aforementioned active group-containing particles, when in a form soluble in water, to assume a state swelled to the highest degree at which the dissolution is barely avoided and, when in a form having the solubility in water repressed such as by a crosslinking reaction, to assume a state swelled to the highest possible degree, allowing the swelled particles to be thoroughly dispersed in a dilute aqueous solution of the aforementioned active hydrogen-containing high molecular substance, stirring the resultant dispersion at temperatures within the range of from 10° to 90° C., preferably from 20° to 40° C., for one to five hours, when necessary, in the presence of a catalyst, and thereafter allowing the stirred dispersion to stand at rest thereby giving rise to the coated particles of active substance of the present invention in the form of a precipitate.

In this case, in order to give the cores a coat of uniform thickness, the concentration in the aforementioned aqueous solution of the active hydrogen-containing substance is desirable to fall within the range of from 1% to 5%.

The coated particles of active substance obtained as described above may be optionally modified, depending on the nature of the high molecular compound forming the protective layer, with heat or with an alcohol or other suitable chemical to complete the coating. They are then washed thoroughly with water and thereafter retained, preferably in a wetted state, in a tightly closed container until they are removed immediately before use.

Since the active group present on the surface of the cores has been inactivated by the high molecular compound of the protective layer, the coated particles of active substance obtained by this invention do not induce the undesirable side effect due to the active group on the surface of the cores. By contrast, the active group present within the cores retains its activity to the highest possible level. Thus, the method of this invention can be utilized extensively for the preparation of medicines and other similar preparations.

Now, the present invention will be described more specifically with reference to working examples.

EXAMPLE 1

In 500 ml of water, 70 g of particles of dialdehyde starch obtained by oxidizing particles of potato starch were dispersed and stirred therein at 50° C. for about three hours. Consequently, the particles of dialdehyde starch were swelled to the highest degree. A 100-ml portion of the water containing the particles of dialdehyde starch was placed in a container having an inner volume of 1 liter and diluted with 400 ml of added water. To the diluted dispersion, an aqueous solution (containing 40 g of polyvinyl alcohol in 400 ml of water) was added while under stirring. The resultant dispersion was acidified by addition of 5 ml of concentrated sulfuric acid and left to stand at 40° C. for five hours to induce a reaction. After the reaction, the solution was left to stand and the supernatant which consequently occurred was discarded. The solid precipitate was washed repeatedly with water. Thus, with only the aldehyde group on the surface of the cores allowed to react with the hydroxyl group of the polyvinyl alcohol to produce acetal, there were consequently obtained, in the form of a precipitate, the particles of dialdehyde starch coated with the inactivated polyvinyl alcohol.

EXAMPLE 2

In 500 ml of water, 70 g of particles of dialdehyde starch obtained by oxidizing particles of potato starch were dispersed and stirred therein at 50° C. for about three hours. Consequently, the particles of dialdehyde starch were swelled to the highest degree. A 100-ml portion of the dispersion containing the particles of dialdehyde starch was placed in a container having an inner volume of 1 liter. It was diluted with 400 ml of added water. To the diluted dispersion, 50 ml of an aqueous 1% gelatine solution was added while under stirring and then held at 30° C. for five hours to induce a reaction. At the end of this reaction, 100 ml of ethyl alcohol was stirred in the dispersion at 30° C. for 30 minutes. The mixture was left to stand and the supernatant which consequently occurred was discarded. The solid precipitate was repeatedly washed with water. Thus, with only the aldehyde group on the surface of the cores allowed to react with the free amino group or hydroxyl group of gelatin, there were consequently obtained, in the form of a precipitate, the particles of dialdehyde starch coated with inactivated gelatin.

EXAMPLE 3

In 500 ml of water, 70 g of particles of dialdehyde starch obtained by oxidizing potato starch were dispersed and stirred at 50° C. for about three hours. Consequently, the particles of dialdehyde starch were swelled to the highest degree. A 200-ml portion of the dispersion containing the particles of dialdehyde starch was placed in a container having an inner volume of 1 liter. It was diluted with 400 ml of added water. To the diluted dispersion, 10 ml of an aqueous 5% albumin solution was added while under stirring and then held at 20° C. for five hours to induce a reaction. At the end of the reaction, the dispersion was repeatedly washed with water. The reaction product was dispersed in 1 liter of water and simultaneously stirred and heated at 80° C. for 30 minutes. The hot aqueous dispersant was then left to stand and the supernatant which occurred consequently was removed. Thus, with only the aldehyde group on the surface of cores allowed to react with the free amino group or hydroxyl group, there were obtained, in the form of a precipitate, the particles of dialdehyde starch coated with inactivated albumin.

EXAMPLE 4

In water, 500 g of particles obtained by oxidizing, with potassium iodate, commercially available Sephadex (a product obtained by three-dimensionally cross-linking soluble dextran with epichlorohydrin) were dispersed and stirred for 24 hours. A 100-g of the oxide swelled with water was dispersed in 500 ml of an aqueous 2% polyacrylamide (having a molecular weight of 500,000 to 1,000,000) solution and held at 25° C. for five hours to induce a reaction. At the end of the reaction, the supernatant was removed and the residue was repeatedly washed with water. Thus, with only the aldehyde group on the surface of the cores allowed to react with the free amino group of the polyacrylamide, there were consequently obtained, in the form of a precipitate, the particles of oxidized Sephadex coated with inactivated polyacrylamide (particles of crosslinked dialdehyde dextran coated with a film of polyacrylamide).

What is claimed is:

1. Particles of an active substance, each comprising: a core formed of a high molecular weight substance containing at least one aldehyde group obtained by oxidizing a polysaccharide and an inactive protective coat formed of the reaction product of said high molecular weight substance with a high molecular weight substance containing active hydrogen containing hydroxyl or amino groups applied to the surface of the core.

2. The particles of claim 1, wherein said polysaccharide has at least two adjoining hydroxyl groups per molecular unit thereof.

3. The particles of claim 1, wherein said oxidized polysaccharide is oxidized cellulose, oxidized starch, oxidized crosslinked dextran, oxidized dextrin, oxidized mannan or oxidized alginic acid.

4. The particles of claim 1, wherein said high molecular weight substance containing active hydrogen atoms is a protein, a polyvinyl alcohol, a polyacrylamide or a polymethacrylamide.

5. The particles of claim 4, wherein said protein is gelatin.

6. Particles of an active substance, each comprising:
a core formed of oxidized cellulose, oxidized starch, oxidized crosslinked dextran, oxidized dextrin, oxidized mannan or oxidized alginic acid and an inactive protective coat which is the reaction product of said oxidized core material with a protein, a polyvinyl alcohol, a polyacrylamide or a polymethacrylamide applied to the surface of said core.

7. A method for the manufacture of the particles of claim 1, comprising: swelling particles of a high molecular weight substance containing at least one aldehyde group obtained by oxidizing a polysaccharide; dispersing said swelled particles in an aqueous solution of a high molecular weight substance containing active hydrogen atoms as hydroxyl groups or amine groups; stirring said particles in solution at a temperature of 10° C. to 90° C. for about 1 to 5 hours; and thereafter, allowing said stirred dispersion to stand.

8. The method of claim 7, wherein said polysaccharide had at least two adjoining hydroxyl groups per molecular unit thereof.

9. The method of claim 7, wherein said high molecular weight substance containing active hydrogen atoms is at least one member selected from the group consisting of proteins, polyvinyl alcohol, polyacrylamide and polymethacrylamide.

10. The method of claim 7, wherein the temperature of stirring ranges from 20° C. to 40° C.

11. Particles of an active substance, each comprising:
a core formed of a dialdehyde derivative of a polysaccharide prepared by oxidizing said polysaccharide consisting of molecular units which contain at least two adjacent hydroxyl groups and an inactive protective coat formed of the reaction product of said dialdehyde derivative with a high molecular weight substance containing active hydrogen atoms as hydroxyl or amino groups applied to the surface of the core.

* * * * *